(12) United States Patent
Iturriaga Zagal

(10) Patent No.: US 12,654,150 B2
(45) Date of Patent: Jun. 16, 2026

(54) METHOD FOR OBTAINING A MODIFIED COLLAGEN ABSORBENT PRODUCT FROM LEATHER

(71) Applicant: Oilkontrol Products, S. L., Alicante (ES)

(72) Inventor: Francisco Fernando Iturriaga Zagal, Alicante (ES)

(73) Assignee: OilKontrol USA, Inc, Doral, FL (US)

( * ) Notice: Subject to any disclaimer, the term of this patent is extended or adjusted under 35 U.S.C. 154(b) by 594 days.

(21) Appl. No.: 17/413,018

(22) PCT Filed: Feb. 13, 2019

(86) PCT No.: PCT/ES2019/070079
§ 371 (c)(1),
(2) Date: Jun. 11, 2021

(87) PCT Pub. No.: WO2020/165467
PCT Pub. Date: Aug. 20, 2020

(65) Prior Publication Data
US 2022/0072507 A1      Mar. 10, 2022

(51) Int. Cl.
| | |
|---|---|
| *B01J 20/24* | (2006.01) |
| *B01J 20/28* | (2006.01) |
| *B01J 20/30* | (2006.01) |
| *C07K 1/00* | (2006.01) |
| *C07K 14/78* | (2006.01) |
| *C14B 13/00* | (2006.01) |
| *F26B 3/04* | (2006.01) |
| *F26B 21/35* | (2026.01) |

(52) U.S. Cl.
CPC ......... *B01J 20/24* (2013.01); *B01J 20/28011* (2013.01); *B01J 20/3078* (2013.01); *C07K 14/78* (2013.01); *F26B 3/04* (2013.01); *F26B 21/35* (2026.01)

(58) Field of Classification Search
CPC .. B01J 20/24; B01J 20/28011; B01J 20/3078; C07K 14/78; C07K 1/00; F26B 3/04; F26B 21/10; C14B 13/00
See application file for complete search history.

(56) References Cited

U.S. PATENT DOCUMENTS

| | | | | | |
|---|---|---|---|---|---|
| 4,169,052 | A | * | 9/1979 | Bocard | C09K 3/32 |
| | | | | | 210/691 |
| 5,731,418 | A | * | 3/1998 | Jain | B01J 20/22 |
| | | | | | 530/356 |

FOREIGN PATENT DOCUMENTS

ES          467778 A1      6/1980

OTHER PUBLICATIONS

Wu et al., Journal of Cleaner Production, (2017), v. 148, p. 158-173.*

* cited by examiner

*Primary Examiner* — Yong L Chu
(74) *Attorney, Agent, or Firm* — Sanchelima & Associates, P.A.; Christian Sanchelima; Jesus Sanchelima

(57) ABSTRACT
The invention relates to a method for obtaining a modified collagen absorbent product from leather, which comprises aerating flat pieces of leather during a time period of between 15 and 45 days; collecting the pieces with an initial relative humidity value of 45% or less; grading the pieces by size; obtaining pieces with a maximum final length of between 0.5 and 1.5 mm; placing the pieces in a drying oven; applying heat in the drying oven so that the pieces are exposed to a temperature of 285° C. or less during a time period; controlling the temperature applied during the time period so that the relative humidity is reduced to a final value of between 0.5% and 5% in the pieces; reducing the temperature of the pieces to an ambient temperature; and obtaining the modified collagen absorbent product from leather.

17 Claims, 1 Drawing Sheet

METHOD FOR OBTAINING A MODIFIED COLLAGEN ABSORBENT PRODUCT FROM LEATHER

1. FIELD OF THE INVENTION

The present invention is related to the industry dedicated to producing products that absorb substances such as hydrocarbons, vegetable oils, and synthetic oils. More specifically, the present invention is related to the industry dedicated to producing these products from leather scraps.

2. DESCRIPTION OF THE RELATED ART

Presently, the need to take care of the environment is widely known. Notably by absorbing spilled harmful substances. These substances include hydrocarbons, vegetable oils, and synthetic oils. Said substances can be found to be detrimentally spilled in liquid media. For example, oceans, seas, lakes, swamps, and rivers. Likewise, these substances are found to be harmful when spilled on solid media, such as soil, cement floors, or any other solid material for this purpose.

To carry out the absorption of said substances, it is known to obtain products from leather scraps. Initially a method or procedure was used that consisted of exposing the leather remains to the open sky for drying. To do this, at least one person with very simple tools was dedicated to removing said remains to standardize the drying of the leather. This solution has the drawback of being dependent on climate conditions. This makes it difficult to produce the product. This solution is also undesirable as it takes an extended period of time, even months to implement.

Nowadays, to expedite the process, unnatural means are used for drying previously collected leather scraps. The employed non-natural means allows the drying of the leather to obtain a result not dictated by climatic or geographical conditions. These non-natural means consist of using objects such as ovens so that the leather is exposed to temperatures above 500° C., which considerably accelerates drying. This solution, however, results in obtaining absorbent products of poor quality. That is products that can be improved upon.

Given the described disadvantages or limitations presented by the currently existing solutions, a new solution is necessary. A solution that allows for obtaining the product to absorb the mentioned substances in a controlled and timely manner without sacrificing the quality of the product.

SUMMARY OF THE INVENTION

The present invention provides a method, or procedure, to obtain a modified collagen absorbent product from leather. To meet this objective and solve the technical problems discussed, additional advantages may be derived later.

The present method comprises the steps of aerating flat leather pieces with a molecular structure for a period of time between 15 and 45 days. Leather pieces with an initial value of relative humidity equal to or less than 45% are then collected. A classification of leather pieces by size is performed. Then leather pieces with a maximum final length of between 0.5 and 1.5 mm, and preferably between 0.75 and 3 mm are obtained. The leather pieces are later put in a drying oven. The drying oven applies heat to the leather pieces at a temperature equal to or lower than 285° C. for a predetermined period of time. This temperature is applied and controlled during the predetermined period of time so that the relative humidity of the leather pieces is reduced to a final value between 0.5% and 5%. After which, the temperature of the leather pieces is reduced to room temperature. This is done in addition to the stage of disposing or obtaining the product from leather.

The modified collagen product obtained has hollow cells so that it can store or retain all kinds of hydrocarbons and oils, both vegetable and synthetic. The modified collagen product obtained can absorb, by capillarity, all kinds of hydrocarbons and oils while being hydrophobic.

Preferably, the initial value of relative humidity is equal to or less than 35%. Additionally, the classification of the pieces by size is carried out by means of mechanical shaking.

In the present method, the leather pieces with a maximum intermediate length of between 0.3 and 3 cm are obtained before being obtained according to the maximum final length. Likewise, between obtaining the leather pieces according to the maximum intermediate length and according to the maximum final length, another classification of the pieces by size is possible. Preferably by means of another mechanical shaking.

Preferably, the drying oven is made of stainless steel and or galvanized steel. Additionally, or alternatively, the drying oven has a longitudinal configuration such that the leather pieces are displaced longitudinally along it during the application of the temperature.

Also, the drying oven preferably has fins to remove and move the leather pieces along it during the application of temperature. Additionally, or alternatively, the drying oven has a particle filter arranged to collect particles generated by the application of heat to the leather pieces.

In the present method, the temperature in the drying oven can be detected so that regulation is carried out to keep the temperature of the leather pieces within a desired range. The period of time of application of heat is dependent on the applied temperature and the relative humidity of the leather pieces. Preferably, the temperature reduction is carried out by exposure to room temperature.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
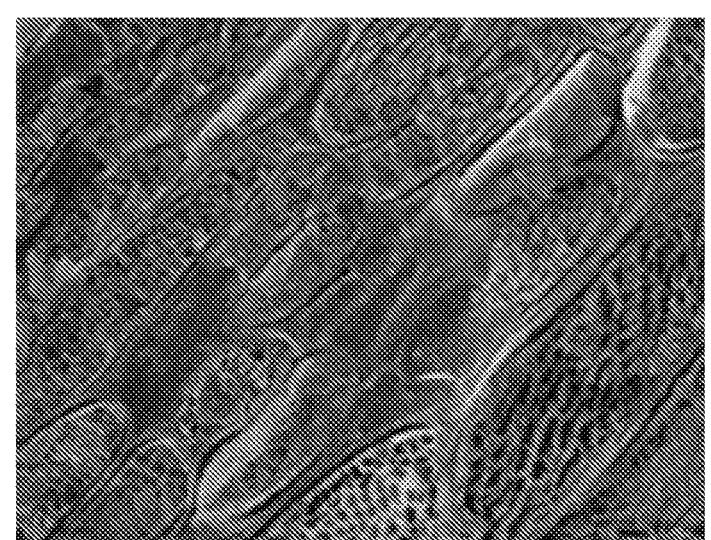
FIG. 1 shows an enlarged view of collagen located on a piece of leather before applying the method to obtain an absorbent product of modified collagen from leather.

The present invention relates to a method of obtaining a modified collagen absorbent product from leather. Preferably, the method involves recycling organic waste derived from a tanning process. In which collagen in the skin is stabilized by tanning agents. In this way, the method comprises collection of pieces or shavings of leather from a tannery. Thus, these pieces or shavings of leather are used to obtain the modified collagen product instead of going to a landfill.

The leather pieces are exposed in such a way that they are subjected to natural aeration for a period of time. As such, the leather pieces are arranged outdoors or exposed to the environment so that the leather pieces are in contact with nature. Optionally, the leather pieces are periodically removed to provide natural aeration evenly.

The time period for aeration is preferably between 15 and 45 days. More preferably it can be between 20 and 40 days. Most preferably it is between 22 and 33 days. The leather pieces have a starting humidity according to a starting value. This is unknown before the leather pieces are exposed to said natural aeration. The time period is additionally dependent on an initial value of relative humidity. This is done so that the application of natural aeration ends with the initial value of relative humidity. This value is preferably equal to or less than 45%. More preferably equal to or less to 40%. Even more preferably equal to or less than 35%. Most preferably equal to or less than 30%.

The method comprises an initial classification of the pieces by size. The method comprises performing an initial mechanical shaking so that the leather pieces are identified and selected according to a first size. This first size is defined such that it is a maximum intermediate length of between 0.3 and 3 cm, and more preferably between 0.5 and 2 cm.

To obtain the leather pieces according to the first size, a first reduction in the size of said pieces is applied, totally or partially. Preferably, this reduction in the size of the leather pieces is carried out by grinding. Thus, the reduction, or grinding, is preferably applied only to leather pieces with the maximum intermediate length greater than 3 cm, and more preferably greater than 2 cm. Thus, a first uniformity is obtained in the size of the leather pieces.

The method comprises a second classification of the leather pieces by size. The method includes performing a second mechanical shaking so that the leather pieces are identified and selected according to a second size. This second size is defined as a maximum final length of between 0.5 and 5 mm, and more preferably between 0.75 and 3 mm.

To obtain the leather pieces according to the second size, a second reduction in the size of said leather pieces is applied, totally or partially. Preferably, this reduction in the size of the leather pieces is carried out by grinding. In this case, an impact crusher is used. Thus, the reduction, or grinding, is preferably applied only to the leather pieces with the maximum final length greater than 5 mm, and more preferably greater than 3 mm. Thus, a second uniformity in the size of the leather pieces is achieved.

Performing the first classification and the second classification, in addition to the first and second reduction in the size of the leather pieces, provides a total or practically total uniformity in the final size achieved. The more uniform the size of the leather pieces, the more uniform the quality of the final product obtained. The leather pieces are also obtainable according to an appropriate size applying only one of said classifications together with the corresponding reduction. This reduces the total application time of the present method.

The method includes dehydration of the leather pieces. For this, the leather pieces are introduced into a drying oven. While in the drying oven the leather pieces are subjected to hot air flow. Preferably, air is applied so that the leather pieces are arranged with a temperature range between 120° C. and 285° C. More preferably between 155° C. and 250° C. And most preferably between 185° C. and 220° C.

The oven temperature is controlled to ensure the temperature of the leather pieces during their dehydration. The temperature is maintained within the previously indicated temperature ranges. Preferably, the controlled temperature is carried out at multiple points in the container of the pieces of leather.

The drying oven used is elongated with a longitudinal configuration for a progressive and continuous advancement or displacement of the leather pieces from one end of the drying oven to another end. In accordance with the containment part of the leather pieces during their dehydration, the aforementioned drying oven includes fins with a double function.

On one side the fins are arranged together with a rotational displacement of the containment portion. Said containment portion arranged with respect to an imaginary central longitudinal axis of the containment portion of the leather pieces during their dehydration. Thereby moving the leather pieces along the longitudinal axis of said containment portion.

On the other side, the flaps are arranged together with a rotational displacement of the containment portion with respect to its imaginary central longitudinal axis. The flaps separate the leather pieces from each other for a more uniform exposure to the hot air flow. Preferably, the drying oven is arranged in a horizontal, or substantially horizontal arrangement, according to said imaginary central longitudinal axis of the part for containing the leather pieces during their dehydration.

The drying oven used is preferably made of stainless steel and or galvanized steel. That is to say, the oven is constituted or manufactured according to materials resistant to oxidation generated by moisture or steam resulting from the drying of the leather pieces. Additionally, using the drying oven being composed of stainless steel and or galvanized steel provides an adequate movement of the leather pieces along it.

Also, in order to contribute to caring for the environment, the drying oven has filtering means, such as a particle filter. In this way, the oven is configured to filter gases and removable fluids in the drying of leather pieces. Thus, harmful residues or substances are prevented from polluting the environment. Accordingly, the present method obtains the modified collagen product cleanly and sustainably. This is achieved since the filtering means only creates a water vapor byproduct from the drying of the leather pieces.

This stage of drying or dehydration of the leather pieces is carried out in such a way that their relative humidity is reduced to a final value preferably between 0.5% and 8%. More preferably between 0.9% and 5%. Even more preferably between 1.5% and 4%. And most preferably 3% or about 3%.

The leather pieces are comprised of collagen fibers. FIG. 1 shows an enlarged view of one of the leather pieces before the application of the present method demonstrating a location of the collagen fibers.

Collagen has physical properties, among which is hydrophilicity. Meaning it turns out to have a tendency to interact with or dissolve in water, or another polar substance. These molecules are capable of hydrogen bonding and are generally polarized. Polar and nonpolar molecules are known as hydrophilic and hydrophobic, respectively. Also, collagen is hydrophilic, that is, it is a substance that has an affinity for water. In a solution or colloid, the hydrophilic molecules are themselves lipophobic; that is, they cannot be mixed with lipids or fats.

Accordingly, the described drying or dehydration steps result in denaturation of the collagen fiber of the leather pieces. This denaturation entails an alteration or modification of the internal and proper structure of collagen. When drying, or dehydration, is carried out this gives rise to this

Figure 2:
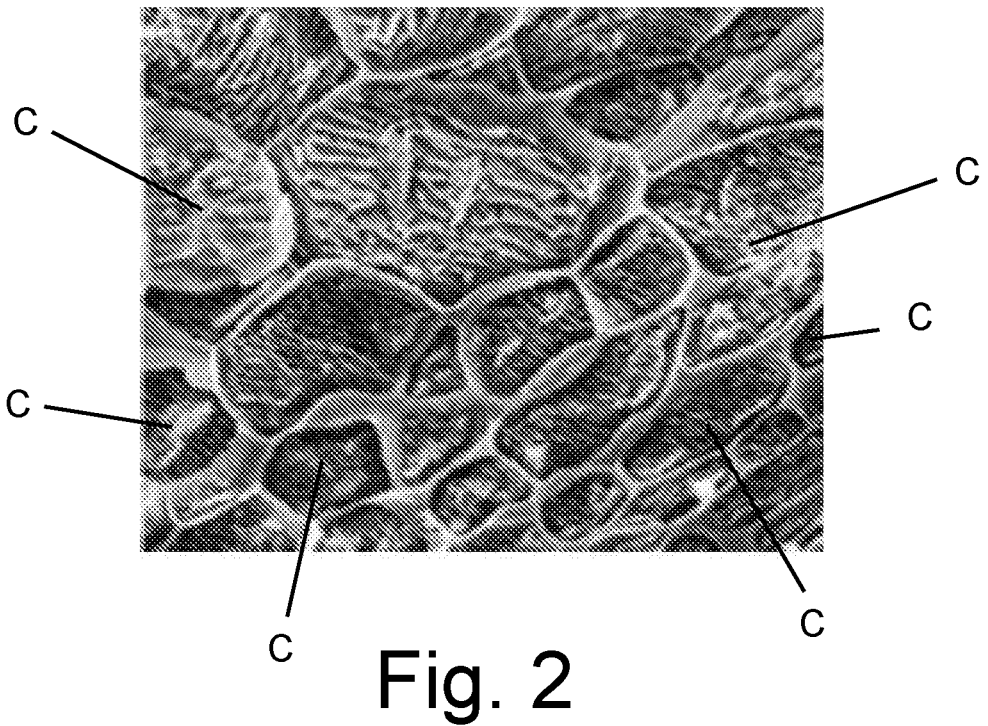
FIG. 2 shows an enlarged view of the modified collagen product obtained after applying the method for obtaining a modified collagen absorbent product from leather.

5 modification by breaking a chain of collagen itself. Thus, changing the molecular structure in such a way that it ceases to have the physical property of hydrophilicity so that collagen becomes hydrophobic in a physicochemical context. Collagen is modified in such a way that it is repelled by water, as well as becomes immiscible with water. Thus, the product obtained is endowed with a flotation capability in water. This modification results in the collagen behaving as hollow cells (C) so that they can absorb, by capillarity, and store or retain all types of hydrocarbons and oils, both vegetable and synthetic. See FIG. 2.

Thus, collagen acquires properties that make it an oleophilic substance or product, in addition to being hydrophobic. The modified collagen product obtained has an absorption capacity of up to 8 times its weight, according to ASTM F/726 analysis.

Additionally, the modified collagen product obtained has a specific gravity of approximately 0.8 or 0.9, an ash content of approximately 4% and inert matter of approximately 0.5%. The modified collagen absorbent product obtained is also flame retardant. In other words, it does not generate flames, charring at 280° C.; and is biodegradable.

To provide an improved generation of the hollow cells (C), the leather pieces are left to rest at room temperature for progressive and continuous cooling. Once they have the relative humidity according to the final desired value. When the temperature of the leather pieces corresponds to the ambient temperature, preferably between 15° C. and 25° C. The leather pieces, or the absorbing product of collagen modified from leather, is ready to be packaged, stored, and or transported for distribution.

The packaging is preferably carried out in such a way that the absorbent product of collagen modified from leather is placed in bags. These bags are comprised of recycled paper. According to an exemplary embodiment, and in accordance with the steps described, acquisition of raw material is initially carried out, that is, the collection of the leather pieces or shavings. Afterward the raw material is placed in the open for the corresponding period of time so that the natural aeration of said raw material takes place.

Preferably, after natural aeration fulfills the conditions described above, the raw material is collected and subjected to the first size classification. Then the first mechanical shaking is performed so that the leather pieces are identified and selected according to the first size.

After the first classification, the raw material is introduced into a large capacity dispenser, accumulator, or feeder. Preferably of at least 1,000 Kg. More preferably of at least 1,500 Kg. And most preferably of at least 2,000 Kg.

Preferably by means of an endless screw, the raw material is transferred from the accumulator or metering feeder to the drying oven. This transfer is done in a portioned manner. Once in the drying oven, the raw material is kept in it until the relative humidity reaches the final value according to what has been previously described.

Then, once the final value is reached, the raw material is transported to be ground so that the first size reduction is carried out, preferably by means of a grinder. Preferably this grinder is known as a TT-160 grinder. This transport preferably takes place through one or more rubber belts. After the first reduction, the resulting leather product is conveyed for additional grinding so that the second size reduction is carried out, preferably by another grinder. This transport is preferably carried out through one or more rubber belts in the "L" position.

After said second size reduction said leather product is obtained according to the second size. This leather product that was ground according to the desired maximum final length is displaced preferably by another endless screw, towards an additional rubber belt. Thus, the ground leather product is distributed to one, two or more silos so that it is stored waiting to be packaged.

Subsequently, the ground leather product is transported, preferably by an endless screw, to be packaged. Once the ground leather product, which corresponds to the modified collagen product, has been packaged, it is ready to be distributed to intermediate or final consumers.

In view of the described embodiment, it is clear that the described steps can be carried out in different orders of succession. It should be understood that some steps may be omitted, such as the first classification, the first reduction, the second classification, and or the second reduction. Depending on the size of the leather pieces that are obtained according to the second size. As such, the drying or dehydration stage can take place before or after obtaining the leather pieces according to said second size.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A method to obtain a modified collagen absorbent product from leather, characterized in that the method comprises the steps of:
   a. aerating leather pieces each having a molecular structure, for a period of 15-45 days;
   b. then collecting said leather pieces with an initial value of relative humidity equal to or less than 45%;
   c. then crushing the aerated leather pieces, resulting in aerated leather pieces of similar size;
   d. then obtaining the leather pieces with a final length between 0.5-3 mm;
   e. then dehydrating resulting aerated and crust leather pieces in a drying oven, said drying oven has a longitudinal configuration with fins arranged together and attached to an interior surface of a containment portion, wherein said fins extend lengthwise along a longitudinal axis thereof, wherein the containment portion rotates about an imaginary central longitudinal axis such that the fins rotate the leather pieces during the application of temperature as the leather pieces are dehydrating; wherein dehydrating resulting aerated and crust leather pieces in the drying oven comprises: subjecting the leather pieces to hot air flow in the drying oven;
   f. then reducing the temperature of the leather pieces to a room temperature; thereby resulting in denaturation of the collagen fiber of the leather pieces, said denaturation entailing a modification of an internal molecular structure of collagen by breaking a collagen chain, changing the internal molecular structure such that the collagen becomes hydrophobic, wherein the collagen is modified to be repelled by water and immiscible with water, and causing the collagen to behave as hollow cells capable of absorbing, by capillarity, and storing hydrocarbons and oils; and
   g. obtaining a hydrophobic and oleophilic absorbent product of collagen modified from leather.

2. The method according to claim 1, characterized in that the initial value of relative humidity is equal to or less than 35%.

3. The method according to claim 1, characterized in that the classification of the pieces by size is carried out by means of mechanical shaking.

4. The method according to claim 3, characterized in that the leather pieces are obtained with an intermediate length of between 0.3-3 cm.

5. The method according to claim 4, characterized in that between obtaining the leather pieces according to the intermediate length and according to the final length, another classification of the pieces by size is carried out by means of another mechanical shaking.

6. The method according to claim 5, characterized in that the final length obtained is between 0.75-1.5 mm.

7. The method according to claim 6, characterized in that the drying oven is made of stainless steel and/or galvanized steel.

8. The method according to claim 7, characterized in that the drying oven has a longitudinal configuration such that the leather pieces are longitudinally arranged along said drying oven during the application of the temperature.

9. The method according to claim 8, characterized in that the drying oven has fins to remove and move the leather pieces along said drying oven during the application of the temperature.

10. The method according to claim 9, wherein the temperature in the drying oven is detected so that regulation is carried out to maintain the temperature of the leather pieces within a desired range.

11. The method according to claim 10, characterized in that the drying oven has a particle filter configured to collect particles generated by the application of heat to the leather pieces.

12. The method according to claim 11, characterized in that the period of time of application of heat is dependent on the applied temperature and the relative humidity of the leather pieces.

13. The method according to claim 12, characterized in that before the leather pieces are introduced into the drying oven, the leather pieces have the final length.

14. The method according to claim 12, characterized in that before the leather pieces with the final length are obtained, the leather pieces are categorized according to the final value of relative humidity.

15. The method according claim 14, characterized in that the reduction in temperature is carried out by exposure to a room temperature.

16. A method to obtain a modified collagen absorbent product from leather, characterized in that the method comprises the steps of:

a. aerating flat leather pieces each having a molecular structure, for a period of 15-45 days; and b. then collecting said flat leather pieces with an initial value of relative humidity equal to or less than 35%; and c. then carrying out a classification of the flat leather pieces by a size, said classification of flat leather pieces accomplished by means of mechanical shaking; and d. then obtaining the flat leather pieces with a maximum final length between 0.75-1.5 mm; and e. then putting the flat leather pieces in a drying oven, said drying oven being constructed of stainless steel and or galvanized steel, wherein said drying oven has a longitudinal configuration to have the flat leather pieces longitudinally arranged along the drying oven, the drying oven including fins to remove and progress the flat leather pieces along said drying oven, said drying oven detecting a temperature so that said drying oven can regulate the temperature of the leather pieces within a range; and f. then applying heat in the drying oven so that the flat leather pieces are subjected to a hot air flow, the drying oven including a particle filter to collect particles generated by the application of heat to said flat leather pieces; and g. regulating the temperature applied during the period of time so that the relative humidity in the flat leather pieces is reduced to a value between 0.5-5%; and h. reducing the temperature of the flat leather pieces to a room temperature; and i. obtaining a hydrophobic and oleophilic absorbent product of collagen modified from leather.

17. A method to obtain a modified collagen absorbent product from leather, consisting of:

a. providing a drying oven being constructed of stainless steel or galvanized steel, wherein said drying oven has a longitudinal configuration, the drying oven including fins, said drying oven including a thermometer to regulate temperature within the drying oven; and b. then aerating flat leather pieces each having a molecular structure, for a period of 15-45 days; and c. then collecting said flat leather pieces with an initial value of relative humidity equal to or less than 35%; and d. then carrying out a classification of the flat leather pieces by a size, said classification of flat leather pieces accomplished by means of mechanical shaking; and e. then obtaining the flat leather pieces with a maximum final length between 0.75-1.5 mm; and f. then arranging said flat leather pieces longitudinally along said drying oven, said fins of the drying oven progressing the flat leather pieces along the drying oven, applying heat in the drying oven so that the flat leather pieces are subjected to a hot air flow, the drying oven including a particle filter to collect particles generated by the application of heat to said flat leather pieces; and g. then regulating the temperature applied during the period of time so that the relative humidity in the flat leather pieces is reduced to a value between 0.5-5%; and h. then reducing the temperature of the flat leather pieces to a room temperature, said reducing the temperature being; and i. then obtaining a hydrophobic and oleophilic absorbent product of collagen modified from leather.

* * * * *